United States Patent
Ngan

(10) Patent No.: US 7,238,847 B2
(45) Date of Patent: Jul. 3, 2007

(54) APPARATUS AND METHOD FOR DETERMINING AND CONTROLLING THE HYDROGEN-TO-CARBON RATIO OF A PYROLYSIS PRODUCT LIQUID FRACTION

(75) Inventor: Danny Yuk-Kwan Ngan, Houston, TX (US)

(73) Assignee: Shell Oil Company, Houston, TX (US)

( * ) Notice: Subject to any disclaimer, the term of this patent is extended or adjusted under 35 U.S.C. 154(b) by 556 days.

(21) Appl. No.: 10/328,424

(22) Filed: Dec. 23, 2002

(65) Prior Publication Data

US 2004/0122276 A1 Jun. 24, 2004

(51) Int. Cl.
*C07G 4/04* (2006.01)
*C10G 9/00* (2006.01)

(52) U.S. Cl. .................. 585/648; 208/106; 208/132; 422/105

(58) Field of Classification Search ................ 585/648; 208/106, 132; 422/105; 436/139, 155
See application file for complete search history.

(56) References Cited

U.S. PATENT DOCUMENTS

| | | | | |
|---|---|---|---|---|
| 3,425,807 A | * | 2/1969 | Levy | 436/158 |
| 4,135,881 A | * | 1/1979 | Bakx et al. | 436/139 |
| 4,400,784 A | | 8/1983 | Funk et al. | 364/500 |
| 4,628,204 A | | 12/1986 | Maes | 250/343 |
| 4,800,279 A | | 1/1989 | Hieftje et al. | 250/339 |
| 4,904,604 A | * | 2/1990 | Kivlen | 436/140 |
| 4,929,335 A | | 5/1990 | Altman et al. | 208/106 |
| 4,940,900 A | | 7/1990 | Lambert | 250/343 |
| 4,963,745 A | | 10/1990 | Maggard | 250/343 |
| 5,082,985 A | | 1/1992 | Crouzet et al. | 585/501 |
| 5,121,337 A | | 6/1992 | Brown | 364/498 |
| 5,145,785 A | | 9/1992 | Maggard et al. | 436/8 |
| 5,223,714 A | | 6/1993 | Maggard | 250/343 |
| 5,243,546 A | | 9/1993 | Maggard | 364/571.02 |
| 5,348,645 A | | 9/1994 | Maggard et al. | 208/209 |
| 5,349,188 A | | 9/1994 | Maggard | 250/339 |
| 5,349,189 A | | 9/1994 | Maggard | 250/339.07 |
| 5,362,965 A | | 11/1994 | Maggard | 250/339.12 |

(Continued)

FOREIGN PATENT DOCUMENTS

EP 801298 A1 10/1997

(Continued)

OTHER PUBLICATIONS

B.P. Ennis et al, "High Temperature—Low Contact Time Pyrolysius Process", Inst. Of Chem. Engr. Symposium Series, vol. 43, Jun. 1975, pp. 12-1-12-10, XP001181269.

(Continued)

*Primary Examiner*—Glenn Caldarola
*Assistant Examiner*—Prem C. Singh

(57) ABSTRACT

A process and apparatus for determining the hydrogen-to-carbon ratio of the liquid fraction of a pyrolysis product by determining the hydrogen-to-carbon ratio of the pyrolysis product gas fraction and subtracting the thus determined value from the determined hydrogen-to-carbon of the hydrocarbon feed to the pyrolysis furnace. The determined value for the hydrogen-to-carbon ratio of the liquid fraction is used as a measure of cracking severity and in the control of the pyrolysis furnace in response to differences between the desired and actual hydrogen-to-carbon ratio of the liquid fraction.

24 Claims, 1 Drawing Sheet

U.S. PATENT DOCUMENTS

Figure 1:
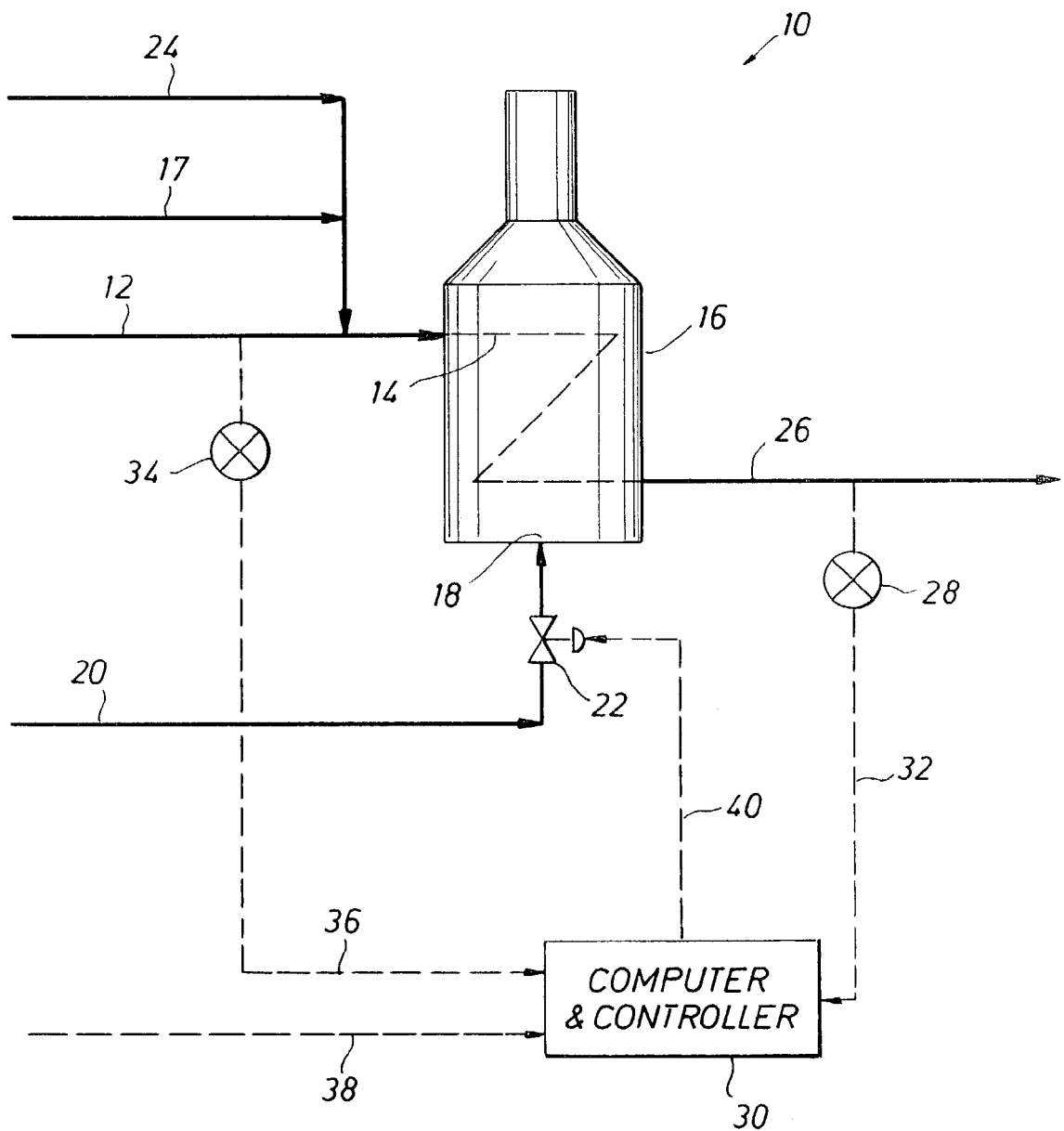

| | | | |
|---|---|---|---|
| 5,370,790 A | 12/1994 | Maggard et al. | 208/142 |
| 5,404,015 A | 4/1995 | Chimenti et al. | 250/339.12 |
| 5,412,581 A | 5/1995 | Tackett | 364/498 |
| 5,430,295 A | 7/1995 | Le Febre et al. | 250/340 |
| 5,446,681 A | 8/1995 | Gethner et al. | 364/554 |
| 5,452,232 A | 9/1995 | Espinosa et al. | 364/498 |
| 5,475,612 A | 12/1995 | Espinosa et al. | 364/500 |
| 5,490,085 A | 2/1996 | Lambert et al. | 364/500 |
| 5,512,751 A | 4/1996 | Murray, Jr. et al. | 250/339.09 |
| 5,572,030 A | 11/1996 | Ranson et al. | 250/339.12 |
| 5,610,836 A | 3/1997 | Alsmeyer et al. | 364/498 |
| 5,641,962 A | 6/1997 | Perry et al. | 250/339.09 |
| 5,681,749 A | 10/1997 | Ramamoorthy | 436/55 |
| 5,684,580 A | 11/1997 | Cooper et al. | 56/301 |
| 5,712,481 A | 1/1998 | Welch et al. | 250/339.12 |
| 5,712,797 A | 1/1998 | Descales et al. | 364/499 |
| 5,740,073 A | 4/1998 | Bages et al. | 364/499 |
| 5,763,883 A | 6/1998 | Descales et al. | 250/339.09 |
| 5,817,517 A | 10/1998 | Perry et al. | 436/55 |
| 5,840,582 A | 11/1998 | Ngan | 436/55 |
| 5,861,228 A | 1/1999 | Descales et al. | 436/171 |
| 5,892,228 A | 4/1999 | Cooper et al. | 250/339.12 |
| 5,935,863 A | 8/1999 | Descales et al. | 436/171 |
| 5,956,254 A | 9/1999 | Collins | 364/479.09 |
| 6,070,128 A | 5/2000 | Descales et al. | 702/30 |
| 6,140,647 A | 10/2000 | Welch et al. | 250/339.12 |
| 2003/0006768 A1* | 1/2003 | Kleinberg et al. | 324/303 |

FOREIGN PATENT DOCUMENTS

EP          0946677 B1     7/2002

OTHER PUBLICATIONS

International Search Report, dated May 17, 2004.

* cited by examiner

APPARATUS AND METHOD FOR DETERMINING AND CONTROLLING THE HYDROGEN-TO-CARBON RATIO OF A PYROLYSIS PRODUCT LIQUID FRACTION

This invention relates to a method and apparatus for determining the hydrogen-to-carbon ratio of a liquid hydrocarbon. Another aspect of the invention relates to a method and apparatus for controlling the severity of pyrolysis cracking processes.

A number of processes for the refining and processing of hydrocarbons require knowledge of ratio of hydrogen-to-carbon in either the hydrocarbons being processed and/or produced. Once such process is the production of olefins, in particular lower olefins, by the thermal cracking of hydrocarbon feedstocks.

The thermal cracking, or pyrolysis, of a hydrocarbon feedstock to prepare olefins is a well known technique in the art. The process is operated on a commercial scale to produce olefins, for example ethylene and propylene, in large quantities. A common process for commercial application is one in which the hydrocarbon feedstock is passed through one or more tubes or coils which define a thermal cracking zone of a pyrolysis furnace. Heat input is provided by means of burners.

The properties of the hydrocarbon feedstock and the conditions under which the thermal cracking takes place determine the nature and contents of the product. In general, it is desirable to operate the thermal cracking process so as to minimize the degree of coking. The depth of cracking or degree of conversion in the thermal cracking process is referred to as the cracking severity. The level of coking generally increases as the severity of the thermal cracking increases, until a point is reached at which the level of coke becomes unacceptable. This point is often referred to as the maximum cracking severity, and often represents an optimum point combining a high olefin yield with an acceptable length of time for which the furnace may be operated before the build up of coke requires the furnace to be shut down for decoke.

In the production of olefins on a commercial scale it is often highly desirable to be able to operate the thermal cracking process at or as close as possible to the maximum cracking severity. A number of indicators of cracking severity have been determined for use in controlling commercial thermal cracking processes. Examples of such indicators include the cracking severity index, of use in naphtha cracking, and the molecular collision parameter, used in the thermal cracking of gasoil. Other indicators include the outlet temperature of the thermal cracking tube or coil, and the hydrogen content of the liquid products of the cracking process. A parameter commonly employed in the manufacture of ethylene is the propylene-to-methane ratio (PMR) or the ethylene-to-methane ratio (EMR) of the gaseous product of the thermal cracking process. However, the sensitivity of these indicators to factors such as changes in the hydrocarbon feedstock and to the reliability of the product sampling techniques give rise to problems when using these indicators as part of a thermal cracking process control system.

Accordingly, there is a need for an indicator of cracking severity which is not sensitive to such process parameters as feedstock quality fluctuations and which may be readily incorporated into a process control system. B. P. Ennis et al. ("High Temperature-Low Contact Time Pyrolysis Process," Symposium Series 43, Institute of Chemical Engineers, Harrogate, Eng., June 1975) describe a steam pyrolysis process for the thermal cracking of a wide range of naphtha fractions. Ennis et al. state that a particularly valuable index of pyrolysis severity is the hydrogen-to-carbon atomic ratio in the pyrolysis gasoline product or $C_5$ and heavier ($C_{5+}$) products. Ennis et al. describe this as being a measure of the degree of dehydrogenation of the liquid phase and the resulting tendency for coke formation. Since the calculated hydrogen-to-carbon ratio of the $C_{5+}$ products depends only on the predicted yield of $C_4$ and lighter components and the hydrogen-to-carbon ratio of the feed, Ennis et al. Claim that this severity indicator is an excellent means of comparing selectivity at the same depth of cracking for various pyrolysis reactors or feedstocks.

While Ennis et al. suggest the use of hydrogen-to-carbon ratio of the $C_{5+}$ products to be a useful indicator of cracking severity, there is no disclosure made of how this parameter is to be measured or how it may be used to control a thermal cracking process on a commercial scale. Heretofore, the ratio of hydrogen-to-carbon in the liquid. ($C_{5+}$) hydrocarbon product of a thermal cracking process has been difficult to determine. Typically, in a commercial thermal cracking process, it is calculated on the basis of an analysis of the hydrocarbon feedstock and the gaseous ($C_{4-}$) products, usually obtained after a detailed feed characterization followed by a simulation of the cracking conditions using a model. However, none of the options available are practical if the hydrogen-to-carbon ratio is to be used as a control parameter.

Accordingly, there is a need for a method of determining the hydrogen-to-carbon ratio of a liquid hydrocarbon fraction which may be readily incorporated in a commercial process control system.

Other aspects, objects, and the several advantages of the invention will become more apparent in light of the following disclosure.

According to the invention, a method is provided for determining the hydrogen-to-carbon ratio of the liquid fraction portion of a pyrolysis product that is yielded from a pyrolysis process. The pyrolysis process includes charging a hydrocarbon feed, having a carbon content, a hydrogen content and a known inert gas concentration, to a pyrolysis furnace that is operated under pyrolysis cracking process conditions. The yielded pyrolysis product includes a liquid fraction and a gas fraction. The hydrogen-to-carbon ratio of the liquid fraction of the pyrolysis product is determined indirectly by using the inert gas as an inert tracer to determine the portion of the pyrolysis product that is the gas fraction and then taking the differences in the hydrogen and carbon content of the hydrocarbon feed and the gas fraction to provide the hydrogen and carbon content of the liquid fraction portion of the pyrolysis product. Having the values for the hydrogen and carbon content of the liquid fraction allows for the computation of the hydrogen-to-carbon ratio of the liquid fraction.

According to another invention, the aforedescribed method for determining the hydrogen-to-carbon ratio of the liquid fraction portion of a pyrolysis product is used in the control of the severity of a pyrolysis process by comparing the determined liquid fraction hydrogen-to-carbon ratio with a desired value for the liquid fraction hydrogen-to-carbon ratio to generate a differential value. The pyrolysis cracking process conditions are adjusted appropriately in response to the differential value.

According to yet another invention, apparatus is provided for determining the hydrogen-to-carbon ratio of the liquid fraction portion of a pyrolysis product that is yielded from a pyrolysis furnace. The process system includes a pyrolysis furnace used to thermally crack a hydrocarbon feed to yield a pyrolysis product. Further included is a first analyzer for determining certain properties of the hydrocarbon feedstock and a second analyzer for determining certain properties of the pyrolysis product. A computer is provided for processing the information generated by the first analyzer and the second analyzer to provide a value for the hydrogen-to-carbon ratio of the pyrolysis product liquid.

FIG. 1 is a schematic representation of one embodiment of the inventive pyrolysis process system and system for determining and controlling the hydrogen-to-carbon ratio of the liquid fraction of a pyrolysis product.

The present invention provides a method for determining the hydrogen-to-carbon ratio of the liquid fraction of a pyrolysis product that is yielded from a thermal cracking zone of a pyrolysis cracking process unit. In a pyrolysis or thermal cracking process, a hydrocarbon feedstock is charged to a pyrolysis or thermal cracking furnace whereby the hydrocarbon feed is subjected to pyrolytic or thermal cracking process conditions. A pyrolysis or cracked product is yielded from the pyrolysis furnace.

The hydrocarbon feedstock used in the thermal cracking process of the present invention may be any of the hydrocarbons or hydrocarbon fractions used in conventional thermal cracking processes for the preparation of olefins. Suitable feedstocks range from C4 fractions, such as butane, $C_5$ fractions, such as pentane, as well as gasoline, naphtha, kerosene and gasoil fractions. Hydrocarbon feedstocks as heavy as vacuum gasoils may also be employed. The process of the present invention is particularly suitable for use with gasoline, naphtha, kerosene and heavy/vacuum gasoil fractions, with gasoline, naphtha and heavy/vacuum gasoil fractions being especially preferred feedstocks. The hydrocarbon feedstocks are readily produced, for example, by means of the conventional refining of crude oil. The hydrocarbon feedstock may consist of a single fraction mentioned hereinbefore or a mixture of the fractions.

An advantage of the process of this invention is that fluctuations in the composition and boiling point range of the hydrocarbon feedstock may occur and be accommodated by the control system. That is, the inventive method is particularly useful in determining and controlling the hydrogen-to-carbon ratio of the pyrolysis product liquid fraction even when there are fluctuations or changes in the composition or boiling point range of the hydrocarbon feedstock.

As earlier noted, the hydrocarbon feedstock is subjected to thermal cracking in a thermal cracking zone. Any suitable process arrangement and apparatus can be employed for the purposes of the present invention. A process regime commonly applied on a commercial scale employs tubular reactor coils installed in externally fired heaters. The hydrocarbon feedstock is fed to the tubular reactor coils which define the thermal cracking zone into which heat is supplied. Heating of the coils is typically provided by the combustion of a suitable fuel, such as a hydrocarbon oil or refinery gas. Suitable apparatus for carrying out the thermal cracking are well known in the art. For a general discussion of aspects of the thermal cracking of hydrocarbon feedstocks to yield olefins, reference is made to Kirk-Othmer Encyclopedia of Chemical Technology, Third Edition, Volume 9, pager 400 to 411.

The operating conditions of the thermal cracking zone are dependent upon the specific design of the thermal cracking apparatus and the severity of cracking required. The hydrocarbon feedstock is heated in the thermal cracking zone until a temperature is reached at which the hydrocarbon molecules crack. The temperature required to effect cracking will depend upon the composition and boiling point range of the feedstock. Typical temperatures for the thermal cracking, measured at the outlet of the thermal cracking zone, are in the range of from 750° C. to 950° C., more preferably from 800° C. to 900° C.

The process may be operated at any suitable pressure. The thermal cracking is preferably carried out at a pressure, measured at the outlet of the thermal cracking zone, in the range of from 1 to 5 bar, more preferably from 1 to 3 bar.

The flowrate at which the hydrocarbon feedstock is supplied to the thermal cracking zone will depend upon the specific design of the process apparatus. Within these constraints, any suitable flowrate may be employed. Typical flowrates of the hydrocarbon feedstock in commercial scale units is in the range of from 10,000 kg/hr to 60,000 kg/hr, more preferably from 15,000 kg/hr to 50,000 kg/hr.

The residence time of the hydrocarbon feedstock in the thermal cracking zone will depend upon the apparatus design and the other process operating conditions. Typical residence times for the hydrocarbon feedstock in the thermal cracking zone are in the range of from 0.05 to 1.0 seconds, more preferably from 0.10 to 0.50 seconds.

To aid the thermal cracking process, the hydrocarbon feedstock may be mixed with an inert diluent and the resulting mixture fed to the thermal cracking zone. A most suitable inert diluent is steam. The inert diluent is typically present in weight ratio of diluent-to-hydrocarbon of from 0.1 to 1.0 kg/kg, more preferably from 0.3 to 0.8 kg/kg.

The pyrolysis product yielded from the thermal cracking zone of the pyrolysis process generally comprises a liquid fraction and a gas fraction. The liquid fraction of the pyrolysis product comprises predominantly hydrocarbons having five or more carbon atoms per molecule and the gas fraction of the pyrolysis product comprises predominantly those hydrocarbons having four or less carbon atoms per molecule and gaseous compounds including carbon monoxide, carbon dioxide, hydrogen sulfide, hydrogen and helium.

An essential aspect of the invention is the introduction or addition of a known amount of an inert gas to the hydrocarbon feedstock being charged to the pyrolysis furnace of the process. Any inert gas that can suitably serve as a tracer by passing through the pyrolysis cracking zone unchanged can be used in the invention. Examples of such suitable inert gas include those selected from the group consisting of helium, argon, nitrogen, and neon; primarily, because, they have low solubility in the liquid fraction of the pyrolysis product. The preferred inert gas for use in the invention, however, is helium since it has the lowest solubility in the pyrolysis prodct liquid fraction.

Essentially all of the inert gas introduced with the hydrocarbon feed to the pyrolysis furnace can be recovered along with the gas fraction of the pyrolysis product; and, because the amount of inert gas introduced into the hydrocarbon feedstock and the amount of hydrocarbon feedstock are both known, the portion of the pyrolysis product that is the gas fraction can readily be determined by measuring the concentration of inert gas that is in the gas fraction. The proportion of the pyrolysis product that is the gas fraction is determined by dividing the value for the known amount of inert gas introduced into the hydrocarbon feedstock by the measured value for the inert gas concentration in the gas fraction.

The use of the inert gas tracer permits the on-line analysis of the pyrolysis product gas fraction using conventional analyzer means for analyzing the gas fraction of the pyrolysis product. Suitable on-line analyzers can include, for example, gas chromatographs and mass spectrometers.

To analyze the gas fraction, a sample of the pyrolysis product is cooled and the gas fraction and liquid fraction are separated. The gas fraction can then be analyzed using suitable analyzer means to determine its inert gas concentration and hydrogen-to-carbon ratio, through the component analyses of the gas fraction. As described above, the value for the inert gas concentration permits a determination of the proportion of the pyrolysis product that is the gas fraction and with the measured value for the hydrogen-to-carbon ratio of the gas fraction, the combination of such information can be used to determine the hydrogen content of the gas fraction and the carbon content of the gas fraction.

In the inventive method, the hydrogen-to-carbon ratio of the liquid fraction of the pyrolysis product is determined indirectly by determining the hydrogen and carbon contents of the gas fraction by the method described above and determining, using any suitable analyzer means, the hydrogen and carbon contents of the hydrocarbon feed to the pyrolysis unit and, then, calculating the difference between the gas fraction hydrogen and carbon contents and the hydrocarbon feed hydrogen and carbon contents to provide values for the amounts of hydrogen and carbon that are in the liquid fraction of the pyrolysis product.

Any suitable analyzer means for determining the hydrogen content of the hydrocarbon feed and for determining the carbon content of the hydrocarbon feed can be used. The preferred means or method of analyzing the hydrocarbon feed include the use of any conventional near infrared (NIR) analysis techniques or the use of conventional nuclear magnetic resonance (NMR) analytical techniques. The preferred analytical technique is NIR analysis. It is understood herein that the hydrogen content of the hydrocarbon feed is analyzed by the NIR or NMR analytical techniques with the carbon content being determined by difference. Also, the sulfur content of the hydrocarbon can additionally be measured and used in determining the carbon content.

The use of NIR spectrometric techniques provides certain advantages such as allowing for the quick and direct online analysis of the hydrocarbon feed. The values for the hydrocarbon feed hydrogen content and the hydrocarbon feed carbon content obtained through the use of the online analyzer can be used in the determination by any suitable computation means of the liquid fraction hydrogen content and the liquid fraction carbon content. The liquid fraction hydrogen-to-carbon ratio is determined by using the information relating to the hydrogen and carbon contents of the hydrocarbon feed and the gas fraction of the pyrolysis product obtained by use of the above-described analysis techniques and computing values for the liquid fraction hydrogen content and the liquid fraction carbon content. Having these values permit the calculation of the hydrogen-to-carbon ratio of the pyrolysis product liquid fraction. Any suitable means or method can be used to perform the computations, but it is preferred to use computer means such as conventional computer systems.

In another aspect of the invention, the determined value for the hydrogen-to-carbon ratio for the pyrolysis product liquid fraction can be used as an indicator of the cracking severity and in the control of the thermal cracking furnace. It is recognized that the correlation between thermal cracking zone severity and liquid fraction hydrogen-to-carbon ratio is inverse and that an increase in the thermal cracking zone severity will result in a decrease in the hydrogen-to-carbon ratio of the pyrolysis product liquid fraction and that a decrease in the thermal cracking zone severity will result in an increase in the hydrogen-to-carbon ratio of the pyrolysis product liquid fraction.

It is desirable to operate the thermal cracking furnace so as to provide a liquid fraction hydrogen-to-carbon ratio of as close to one (1.0) as is economically feasible; but, generally, the liquid fraction hydrogen-to-carbon ratio should be controlled to within the range of from about 1.01 to about 1.5 and, more typically, it is controlled to within the range of from about 1.02 to about 1.2 and, most typically, from 1.05 to 1.1. Typical hydrocarbon-to-carbon ratios for a hydrocarbon feed to a pyrolysis cracking unit are in the range of from about 1.6 to about 2.5, more typically from about 1.7 to about 2.2 and, most typically, from 1.8 to 2.0.

In the control of the pyrolysis cracking process conditions there is a predetermined desired thermal cracking severity as represented by a desired hydrogen-to-carbon ratio for the pyrolysis product liquid fraction. To control the pyrolysis process, a comparison is made between the desired liquid fraction hydrogen-to-carbon ratio and the actual liquid fraction hydrogen-to-carbon ratio, as determined in accordance with the inventive method described herein, to provide a differential value. The pyrolysis process conditions are adjusted in response to any differences between the desired and actual hydrogen-to-carbon ratio values.

The differential value can be defined as the difference in the hydrocarbon-to-carbon ratio as determined by subtracting the actual value for the liquid fraction hydrocarbon-to-carbon ratio from the desired value for the liquid fraction hydrocarbon-to-carbon ratio. A negative differential value will require increasing the pyrolysis process cracking severity and a positive differential value will require decreasing the pyrolysis process cracking severity.

While a number of pyrolysis process operating conditions can impact the severity of the thermal cracking conditions, one typical process parameter that is controlled in response to the differential value in hydrogen-to-carbon ratio is the cracking temperature within the thermal cracking zone. The thermal cracking zone temperature is related to and can be monitored by measurement of the temperature of the pyrolysis product at the outlet of the thermal cracking zone. The thermal cracking zone temperature can be controlled by adjusting the firing rate of the burners of the pyrolysis furnace.

Now referring to FIG. 1, presented is a simplified schematic representation of a pyrolysis process system 10 for thermally cracking a hydrocarbon feed. A hydrocarbon feedstock is charged, at a known rate, by way of conduit 12 to cracking furnace tubes or coils 14 of pyrolysis or thermal cracking furnace 16. A diluent steam stream may be introduced into the hydrocarbon feedstock of conduit 12 by way of conduit 17. Thermal cracking furnace 16 is equipped with cracking furnace tubes or coils 14 and burners 18. Thermal cracking furnace 16 defines a heating zone and provides means for thermally cracking the hydrocarbon feed. Cracking furnace tubes or coils 14 define a pyrolysis or thermal cracking zone and provide means for receiving the hydrocarbon feed for heat input into the hydrocarbon feed. Burners 18 define a combustion zone and provide means for combusting a fuel to generate heat for input into the thermal cracking zone defined by cracking furnace tubes or coils 14.

Fuel is introduced to burners 18 through conduit 20. Interposed in conduit 20 is control valve 22, which provides means for controlling the rate of fuel input into burners 18 to thereby control the heat input to the thermal cracking zone defined by cracking furnace tubes or coils 14.

An inert gas, such as helium, is introduced through conduit 24 at a known rate into the diluent steam stream 17 that combines with the hydrocarbon feed being charged to cracking furnace tubes or coils 14 through conduit 12. The pyrolysis product is withdrawn as an effluent from cracking furnace tubes or coils 14 through conduit 26. A sample of the pyrolysis product is removed from conduit 26 for analysis by analyzer 28. Analyzer 28 provides means for analyzing the gas fraction of the pyrolysis product for the inert gas concentration, the fraction that is hydrogen and the fraction that is carbon. To analyze the gas fraction of the pyrolysis product, the pyrolysis product is first separated into its gas fraction and liquid fraction, with the gas fraction being analyzed by analyzer 28. The information generated by analyzer 28 is provided to computer and controller 30 by line 32.

A sample of the hydrocarbon feed is removed from conduit 12 for analysis by analyzer 34. Analyzer 34 provides means for measuring and determining the hydrogen and carbon content of the hydrocarbon feed. The information generated by analyzer 34 is provided to computer and controller 30 by line 36. Computer and controller 30 provides means for processing the input information to compute a value for the hydrogen-to-carbon ratio of the liquid fraction of the pyrolysis product and, further, to provide means to control the cracking severity at which thermal cracking furnace 16 operates in response to changes in the liquid fraction hydrogen-to-carbon ratio.

To control the severity of the cracking process a predetermined value, also referred to as a set point, for the desired hydrogen-to-carbon ratio for the liquid fraction is provided to computer and controller 30 by line 38. Computer and controller 30 processes the information provided by line 32, line 36 and line 38 to compute a value for the hydrogen-to-carbon ratio of the liquid fraction. A differential value between the actual hydrogen-to-carbon ratio of the liquid fraction and the desired hydrogen-to-carbon ratio of the liquid fraction is computed by computer and controller 30 with an output signal, representative of the differential value, being sent by line 40 to control valve 22. Control valve 22 is adjusted in response to the input signal from line 40 to thereby alter the heat input to thermal cracking furnace 16 and, thus, the cracking severity, to ultimately provide a liquid fraction having the desired hydrogen-to-carbon ratio.

While this invention has been described in terms of the presently preferred embodiment, reasonable variations and modifications are possible by those skilled in the art. Such variations and modifications are within the scope of the described invention and the appended claims.

That which is claimed is:

1. In a pyrolysis process in which a known amount of a hydrocarbon feed containing a known amount of an inert gas tracer, a hydrocarbon feed carbon content and a hydrocarbon feed hydrogen content, is charged to a pyrolysis furnace operated under pyrolysis cracking process conditions to yield a pyrolysis product wherein said pyrolysis product comprises a liquid fraction and a gas fraction, wherein said liquid fraction comprises a liquid fraction hydrogen content and a liquid fraction carbon content to thereby provide a liquid fraction hydrogen-to-carbon ratio, and wherein said gas fraction comprises a gas fraction inert gas tracer concentration, a gas fraction hydrogen content and a gas fraction carbon content, a method is provided for determining said liquid fraction hydrogen-to-carbon ratio, said method comprising the steps of:

(a) determining said hydrocarbon feed hydrogen content and said hydrocarbon feed carbon content;

(b) determining said gas fraction hydrogen content and said gas fraction carbon content by
determining said gas fraction inert gas tracer concentration, utilizing the thus determined gas fraction inert gas tracer concentration to determine the proportion of said pyrolysis product that is said gas fraction, and utilizing the thus determined proportion of said pyrolysis product that is said gas fraction in determining said gas fraction hydrogen content and said gas fraction carbon content; and (c) determining said liquid fraction hydrogen-to-carbon ratio by
subtracting the determined value for said gas fraction hydrogen content from the determined value for said hydrocarbon feed hydrogen content to give said liquid fraction hydrogen content,
subtracting the determined value for said gas fraction carbon content from the determined value for said hydrocarbon feed carbon content to give said liquid fraction carbon content, and
calculating the value for said liquid fraction hydrogen-to-carbon ratio.

2. A method as recited in claim 1 wherein:
said determining step (a) is performed either by near infrared spectrometry or by nuclear magnetic resonance.

3. A method as recited in claim 1 wherein:
said determining step (b) is performed either by mass spectrometry or by gas chromatography.

4. A method as recited in claim 1 wherein said determining step (c) is performed by means for computing said liquid fraction hydrogen-to-carbon ratio.

5. In a pyrolysis process in which a known amount of a hydrocarbon feed, containing a known amount of an inert gas tracer, a hydrocarbon feed carbon content and a hydrocarbon feed hydrogen content, is charged to a pyrolysis furnace operated under pyrolysis cracking process conditions to yield a pyrolysis product wherein said pyrolysis product comprises a liquid fraction and a gas fraction, wherein said liquid fraction comprises a liquid fraction hydrogen content and a liquid fraction carbon content to thereby provide a liquid fraction hydrogen-to-carbon ratio, and wherein said gas fraction comprises a gas fraction inert gas tracer concentration, a gas fraction hydrogen content and a gas fraction carbon content, a method is provided comprising the steps of:

(a) determining said gas fraction hydrogen content and said gas fraction carbon content utilizing said inert gas tracer concentration;

(b) determining said hydrocarbon feed hydrogen content and said hydrocarbon feed carbon content; and (c) computing said liquid fraction hydrogen-to-carbon ratio by
using said gas fraction hydrogen content as determined by step (a) and said hydrocarbon feed hydrogen content as determined by step (b) to determine said liquid fraction hydrogen content,
using said gas fraction carbon content as determined by step (a) and said hydrocarbon feed carbon content as determined by step (b) to determine said liquid fraction carbon content, and
computing said liquid fraction hydrogen-to-carbon ratio utilizing the above determined said liquid fraction hydrogen content and the above determined said liquid fraction carbon content.

6. A method as recited in claim 5 wherein:
determining step (b) is performed by use of near infrared spectrometry to provide a first measured value of said hydrocarbon feed hydrogen content and a second calculated value of said hydrocarbon feed carbon content.

7. A method as recited in claim 6 wherein:
determining step (a) is performed by
determining by use of mass spectrometry a third measured value of said gas fraction inert gas tracer concentration;
utilizing said third measured value in computing a first calculated value of the proportion of said pyrolysis product that is said gas fraction; and
utilizing said first calculated value in combination with the mass spectrometric analysis of the hydrogen content and the carbon content of said gas fraction to give a fourth measured value of said gas fraction by hydrogen content and a fifth measured value of said gas fraction carbon content.

8. A method as recited in claim 7 wherein:
computing step (c) is performed by subtracting said fourth measured value from said first measured value to give a second calculated value for said liquid fraction hydrogen content;
subtracting said fifth measured value from said second measured value to give a third calculated value for said liquid fraction carbon contact; and
computing a fourth calculated value for said liquid fraction hydrogen-to-carbon ratio by dividing said second calculated value by said third calculated value to give said liquid fraction hydrogen-to-carbon ratio.

9. In a pyrolysis process in which a known amount of a hydrocarbon feed, containing a known amount of an inert gas tracer, a hydrocarbon feed carbon content and a hydrocarbon feed hydrogen content, is charged to a pyrolysis furnace operated under pyrolysis cracking process conditions to yield a pyrolysis product wherein said pyrolysis product comprises a liquid fraction and a gas fraction, wherein said liquid fraction comprises a liquid fraction hydrogen content and a liquid fraction carbon content to thereby provide a liquid fraction hydrogen-to-carbon ratio, and wherein said gas fraction comprises a gas fraction inert gas tracer concentration, a gas fraction hydrogen content and a gas fraction carbon content, a method is provided for controlling said pyrolysis cracking process conditions, said method comprises the steps of:
 (a) determining by use of near infrared spectrometry a first measured value of said hydrocarbon feed hydrogen content and a second measured value of said hydrocarbon feed carbon content;
 (b) determining by use of mass spectrometry a third measured value of said gas fraction hydrogen content, a fourth measured value of said gas fraction carbon content and a fifth measured value of said gas fraction inert gas tracer concentration;
utilizing said fifth measured value in computing a second calculated value of the proportion of said pyrolysis product that is said gas fraction; and
utilizing said second calculated value in combination with the mass spectrometric analysis of the hydrogen content and the carbon content of said gas fraction to give said third measured value and said fourth measured value;
 (c) computing a first calculated value for said liquid fraction hydrogen-to-carbon ratio;
 (d) comparing said first calculated value to a desired value for said liquid fraction hydrogen-to-carbon ratio to generate a differential value; and
 (e) controlling said pyrolysis cracking process conditions in response to said differential value.

10. A method as recited in claim 9 wherein:
computing step (c) is performed by
subtracting said third measured value from said first measured value to give a third calculated value for said liquid fraction hydrogen content;
subtracting said fourth measured value from said second measured value to give a fourth calculated value for said liquid fraction carbon contact; and
computing said first calculated value by dividing said third calculated value by said fourth calculated value to give said liquid fraction hydrogen-to-carbon ratio.

11. A method as recited in claim 10 wherein:
comparing step (d) is performed by
subtracting said first calculated value from said desired value to give said differential value.

12. A method as recited in claim 11 wherein:
controlling step (e) includes increasing the severity of said pyrolysis cracking process conditions in response to a negative value for said differential value and decreasing the severity of said pyrolysis cracking process conditions in response to a positive value for said differential value.

13. A method as recited in claim 12 wherein said desired value for said liquid fraction hydrogen-to-carbon ratio is in the range of from about 1.0 to about 2.0.

14. A method as recited in claim 13 wherein said pyrolysis cracking furnace includes a thermal cracking zone;
wherein said pyrolysis cracking process conditions include a thermal cracking zone temperature which is representative of the severity of said pyrolysis cracking process whereby increases in said thermal cracking zone temperature provides for an increase in the severity of said pyrolysis cracking process conditions and decreases in said thermal cracking zone temperature provides for a decrease in the severity of said pyrolysis cracking process conditions.

15. A method as recited in claim 14 wherein: controlling step (e) provides for maintaining said thermal cracking zone temperature in the range of from 750° C. TO 950° C.

16. A method as recited in claim 11
wherein said pyrolysis cracking furnace includes a thermal cracking zone;
wherein said pyrolysis cracking process conditions include a thermal cracking zone temperature; and
wherein controlling step (e) includes
 increasing said thermal cracking zone temperature in response to a negative value for said differential value and decreasing said thermal cracking zone temperature in response to a positive value for said differential value.

17. An apparatus for thermally cracking a known amount of a hydrocarbon feed containing a known amount of an inert gas tracer, a hydrocarbon feed hydrogen content and a hydrocarbon feed carbon content, said apparatus comprising:
pyrolysis furnace means defining a thermal cracking zone operated under pyrolysis cracking process conditions, which include a thermal cracking zone temperature, said pyrolysis furnace means provides for cracking said hydrocarbon feed to produce a pyrolysis product comprising a liquid fraction and a gas fraction;
first analyzer means for determining the hydrogen content of said hydrocarbon feed and for determining the carbon content of said hydrocarbon feed;
second analyzer means for determining the inert gas tracer concentration of said gas fraction and for determining the hydrogen concentration of said gas fraction and for determination the carbon concentration of said gas fraction; and computation means for determining the hydrogen-to-carbon ratio of said liquid fraction by using the determined hydrogen content of said hydrocarbon feed and the determined carbon content of said hydrocarbon feed as determined by said first analyzer means, and the determined hydrogen concentration of said gas fraction and the determined carbon concentration of said gas fraction as determined by said second analyzer means using said inert gas tracer concentration.

18. An apparatus as defined in claim 17, further comprising:
comparing means for comparing the determined hydrogen-to-carbon ratio of said liquid fraction as determined by said computation means to generate a differential value between a desired hydrogen-to-carbon ratio for said liquid fraction and the determined hydrogen-to-carbon ratio of said liquid fraction; and
control means for adjusting said thermal cracking zone temperature in response to said differential value.

19. An apparatus as defined in claim 18, wherein said first analyzer means includes a near infrared analyzer.

20. An apparatus as defined in claim 19, wherein said second analyzer means includes a mass spectrometer.

21. A method as recited in claim 1, wherein the inert gas tracer is selected from the group consisting of helium, argon, nitrogen and neon.

22. A method as recited in claim 5, wherein the inert gas tracer is selected from the group consisting of helium, argon, nitrogen and neon.

23. A method as recited in claim 9, wherein the inert gas tracer is selected from the group consisting of helium, argon, nitrogen and neon.

24. An apparatus as recited in claim 17, wherein the inert gas tracer is selected from the group consisting of helium, argon, nitrogen and neon.

* * * * *